US00PP22804P2

(12) United States Plant Patent
Eveleens

(10) Patent No.: US PP22,804 P2
(45) Date of Patent: Jun. 19, 2012

(54) ***GERBERA* PLANT NAMED 'GARLISA'**

(50) Latin Name: *Gerbera hybrida*
Varietal Denomination: Garlisa

(75) Inventor: Jan Leendert Eveleens, Aalsmeer (NL)

(73) Assignee: Florist de Kwakel B.V., Aalsmeer (NL)

( * ) Notice: Subject to any disclaimer, the term of this patent is extended or adjusted under 35 U.S.C. 154(b) by 0 days.

(21) Appl. No.: 12/802,583

(22) Filed: Jun. 9, 2010

(51) Int. Cl.
*A01H 5/00* (2006.01)

(52) U.S. Cl. ..... Plt./357

(58) Field of Classification Search ..... Plt./357
See application file for complete search history.

(56) References Cited

OTHER PUBLICATIONS

UPOV-ROM GTITM, Plant Variety Database 2011/01, GTI Jouve Retrieval Software, Citation for 'Lisa', 2 pp.*

* cited by examiner

*Primary Examiner* — June Hwu
(74) *Attorney, Agent, or Firm* — C. A. Whealy

(57) ABSTRACT

A new and distinct cultivar of *Gerbera* plant named 'Garlisa', characterized by its compact, upright and uniformly mounding plant habit; freely flowering habit; red purple-colored ray florets; upright and strong scapes; and good garden performance.

1 Drawing Sheet

Botanical designation: *Gerbera hybrida.*
Cultivar denomination: 'GARLISA'.

BACKGROUND OF THE INVENTION

The present invention relates to a new and distinct cultivar of *Gerbera* plant, botanically known as *Gerbera hybrida* and hereinafter referred to by the name 'Garlisa'.

The new *Gerbera* plant is a product of a planned breeding program conducted by the Inventor in De Kwakel, The Netherlands. The objective of the breeding program is to create new compact container *Gerbera* plants with numerous inflorescences, good garden performance, frost tolerance and attractive inflorescence coloration.

The new *Gerbera* plant originated from a cross-pollination in March, 2006 in De Kwakel, The Netherlands of a proprietary selection of *Gerbera hybrida* identified as code number B 1064, not patented, as the female, or seed, parent with a proprietary selection of *Gerbera hybrida* identified as code number B 1274, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the spring of 2007.

Asexual reproduction of the new *Gerbera* plant by tissue culture in a controlled environment in De Kwakel, The Netherlands since the spring of 2007 has shown that the unique features of this new *Gerbera* plant are stable and reproduced true to type in successive generations.

SUMMARY OF THE INVENTION

Plants of the new *Gerbera* have not been observed under all possible environmental conditions. The phenotype may vary somewhat with variations in cultural practices and environment such as temperature and light intensity, without, however, any variance in genotype.

The following traits have been repeatedly observed and are determined to be the unique characteristics of 'Garlisa'. These characteristics in combination distinguish 'Garlisa' as a new and distinct cultivar of *Gerbera* plant:

1. Compact, upright and uniformly mounding plant habit.
2. Freely flowering habit.
3. Red purple-colored ray florets.
4. Upright and strong scapes.
5. Good garden performance.

Plants of the new *Gerbera* differ from plants of the female parent selection in the following characteristics:

1. Plants of the new *Gerbera* have smaller leaves than plants of the female parent selection.
2. Plants of the new *Gerbera* are more freely flowering than plants of the female parent selection.
3. Plants of the new *Gerbera* have lighter red purple-colored ray florets than plants of the female parent selection.

Plants of the new *Gerbera* differ from plants of the male parent selection in the following characteristics:

1. Plants of the new *Gerbera* have larger leaves than plants of the male parent selection.
2. Plants of the new *Gerbera* have smaller inflorescences than plants of the male parent selection.
3. Plants of the new *Gerbera* have shorter peduncles than plants of the male parent selection.
4. Plants of the new *Gerbera* have lighter red-colored ray florets than plants of the male parent selection.

Plants of the new *Gerbera* can be compared to plants of the *Gerbera hybrida* 'Fleurie', disclosed in U.S. Plant Pat. No. 22,343. Plants of the new *Gerbera* differ from plants of 'Fleurie' in the following characteristics:

1. Plants of the new *Gerbera* have slightly larger inflorescences than plants of 'Fleurie'.
2. Plants of the new *Gerbera* and 'Fleurie' differ in ray and disc floret color as plants of 'Fleurie' have dark red-colored ray florets and light red-colored disc florets.

Plants of the new *Gerbera* can also be compared to plants of the *Gerbera hybrida* 'Amgerbpink', not patented. Plants of the new *Gerbera* differ from plants of 'Amgerbpink' in the following characteristics:

1. Plants of the new *Gerbera* are more freely flowering than plants of 'Amgerbpink'.
2. Plants of the new *Gerbera* have larger inflorescences than plants of 'Amgerbpink'.
3. Plants of the new *Gerbera* and 'Amgerbpink' differ in ray floret color as plants of 'Amgerbpink' have soft pink-colored ray florets.

Plants of the new *Gerbera* can also be compared to plants of the *Gerbera jamesonii* 'Lisa', not patented. Plants of the new *Gerbera* differ from plants of 'Lisa' in the following characteristics:

1. Plants of the new *Gerbera* are more compact and more uniform than plants of 'Lisa'.
2. Plants of the new *Gerbera* are suitable for container and garden cultivation whereas plants of 'Lisa' are suitable for cut flower cultivation.
3. Plants of the new *Gerbera* and 'Lisa' differ in ray floret color.

BRIEF DESCRIPTION OF THE PHOTOGRAPH

The accompanying photograph illustrates the overall appearance of the new *Gerbera* plant. The photograph shows the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garlisa' grown in a container.

DETAILED BOTANICAL DESCRIPTION

The aforementioned photograph and following observations and measurements describe plants grown during the winter in 19-cm containers in a glass-covered greenhouse in De Kwakel, The Netherlands and under cultural practices and environmental conditions which approximate those generally used in commercial container *Gerbera* production. During the production of the plants, day temperatures ranged from 16° C. to 24° C. and night temperatures ranged from 16° C. to 20° C. Rooted young tissue-cultured plants were four months old when the photograph was taken and eight months old when the description was taken. In the following description, color references are made to The Royal Horticultural Society Colour Chart, Fifth Edition, 2007, except where general terms of ordinary dictionary significance are used.

Botanical classification: *Gerbera hybrida* 'Garlisa'.

Parentage:

*Female, or seed, parent*.—Proprietary selection of *Gerbera hybrida* identified as code number B 1064, not patented.

*Male, or pollen, parent*.—Proprietary selection of *Gerbera hybrida* identified as code number B 1274, not patented.

Propagation:

*Type*.—By tissue culture.

*Time to initiate roots*.—About 2.5 to three weeks at temperatures of 20° C.

*Time to produce a rooted young plant*.—About five to six weeks at temperatures of 20° C. to 26° C.

*Root description*.—Fibrous; white in color.

Plant description:

*Appearance*.—Herbaceous perennial that are typically grown as container or garden plants; compact, upright and uniformly mounding plant habit, roughly globular in shape; leaves arranged in basal rosettes and outwardly arching; dense and bushy habit; inflorescences held above the foliar plane on erect and strong basal scapes; moderately vigorous growth habit.

*Plant height, soil level to top of foliar plane*.—About 15 cm.

*Plant height, soil level to top of inflorescences*.—About 34 cm.

*Plant width*.—About 39 cm.

Foliage description:

*Arrangement*.—Alternate, simple.

*Length*.—About 15 cm.

*Width*.—About 10 cm.

*Shape*.—Oblong.

*Apex*.—Acute to obtuse.

*Base*.—Truncate.

*Margin*.—Irregularly crenate to dentate; sinuses divergent; undulate.

*Texture, upper surface*.—Sparsely pubescent.

*Texture, lower surface*.—Moderately pubescent.

*Venation pattern*.—Pinnate.

*Color*.—Developing leaves, upper surface: Close to 138A. Developing leaves, lower surface: Close to 138C. Fully expanded leaves, upper surface: Close to 137A; venation, close to 144A. Fully expanded leaves, lower surface: Close to 138B; venation, close to 144B.

*Petioles*.—Length: About 10.5 cm. Diameter: About 3 mm. Texture, upper and lower surfaces: Moderately pubescent. Color, upper surface: Close to 144A to 144B. Color, lower surface: Close to 144B to 144C.

Inflorescence description:

*Appearance*.—Semi-double type inflorescence form with narrowly elliptic-shaped ray florets; solitary inflorescences borne on upright and strong scapes above the foliar plane; ray and disc florets arranged acropetally on a capitulum.

*Fragrance*.—None detected.

*Flowering season*.—Plants begin flowering about three months after planting and flower from April to November in outdoor gardens in The Netherlands; plants flower year-round under greenhouse conditions.

*Inflorescence longevity*.—Inflorescences last about two to four weeks on the plant; inflorescences not persistent.

*Quantity of inflorescences*.—Freely flowering habit with about 29 open and developing inflorescences per plant at one time.

*Inflorescence bud*.—Height: About 1.7 cm. Diameter: About 1.8 cm. Shape: Oblate. Color: Close to 138B; towards the base, close to 143B; towards the apex, close to 178A to 178B and 182B.

*Inflorescence size*.—Diameter: About 6.6 cm. Depth (height): About 3.7 cm. Diameter of disc: About 2.5 cm. Receptacle height: About 3 mm. Receptacle diameter: About 3 mm. Receptacle color: Close to 157B to 157C.

*Ray florets*.—Orientation: About 65° from vertical. Length: About 3.1 cm. Width: About 7 mm. Shape: Narrowly elliptic. Apex: Emarginate to obtuse. Base:

Cuneate. Margin: Entire. Texture, upper and lower surfaces: Smooth, glabrous; slightly velvety; longitudinally ridged. Number of ray florets per inflorescence: About 43 arranged in about two whorls. Color: When opening, upper surface: Close to 60C. When opening, lower surface: Close to 59D. Fully opened, upper and lower surfaces: Close to 60C; color does not fade with development.

*Disc florets*.—Arrangement: Massed at center of receptacle. Shape: Tubular, fused. Apex: Acute. Base: Fused. Margin: Entire. Length: About 1.7 cm. Width: About 3 mm. Texture, upper and lower surfaces: Smooth, glabrous. Number of disc florets per inflorescence: About 180. Color, prior to opening: Apex: Close to 150B. Mid-section: Close to 157D. Base: Close to 157C to 157D. Color, when opening: Apex: Close to 63C. Mid-section: Close to 157D. Base: Close to 157D and 155C. Color, fully opened: Apex: Close to 62B and 63D. Mid-section: Close to 157D. Base: Close to 157D and 155C.

*Pappus*.—Number of hairs per floret: About 50. Length: About 6 mm. Diameter: Less than 1 mm. Texture: Soft. Color: Close to 150D.

*Phyllaries*.—Number of phyllaries per inflorescence: About 40 arranged in about two whorls. Length: About 1.3 cm. Width: About 2 mm. Shape: Lanceolate. Apex: Narrowly acute. Base: Cuneate. Margin: Entire. Texture, upper surface: Smooth, glabrous. Texture, lower surface: Densely tomentose. Color, upper surface: Close to 144A. Color, lower surface: Close to 138B; towards the base, close to 143A to 143B.

*Scapes*.—Length: About 37.8 cm. Diameter: Distally, about 3 mm; proximally, about 4.5 mm. Angle: About 10° from vertical. Strength: Strong. Texture: Moderately densely tomentose. Color: Close to 144B; distally, close to 143A to 143B; proximally, close to 145A.

*Reproductive organs*.—Androecium: Present on disc only florets. Quantity per floret: Two. Filament length: About 1.15 cm. Filament color: Close to 155A. Anther shape: Lanceolate. Anther length: About 0.5 mm. Anther color: Close to 13D. Pollen amount: Scarce. Pollen color: Close to 8A. Gynoecium: Present on disc and ray florets. Quantity per floret: One. Pistil length: About 1.1 cm. Stigma shape: Cleft. Stigma color: Close to 200A. Style length: About 1.05 cm. Style color: Close to NN155C. Ovary color: Close to 155A.

*Seed/fruit*.—Seed and fruit production has not been observed.

Disease/pest resistance: Resistance to pathogens and pests common to *Gerberas* has not been observed on plants of the new *Gerbera* grown under commercial production conditions.

Garden performance: Plants of the new *Gerbera* have been observed to have good garden performance and to tolerate wind, rain and temperatures from about −5° C. to about 35° C.

It is claimed:

1. A new and distinct *Gerbera* plant named 'Garlisa' as illustrated and described.

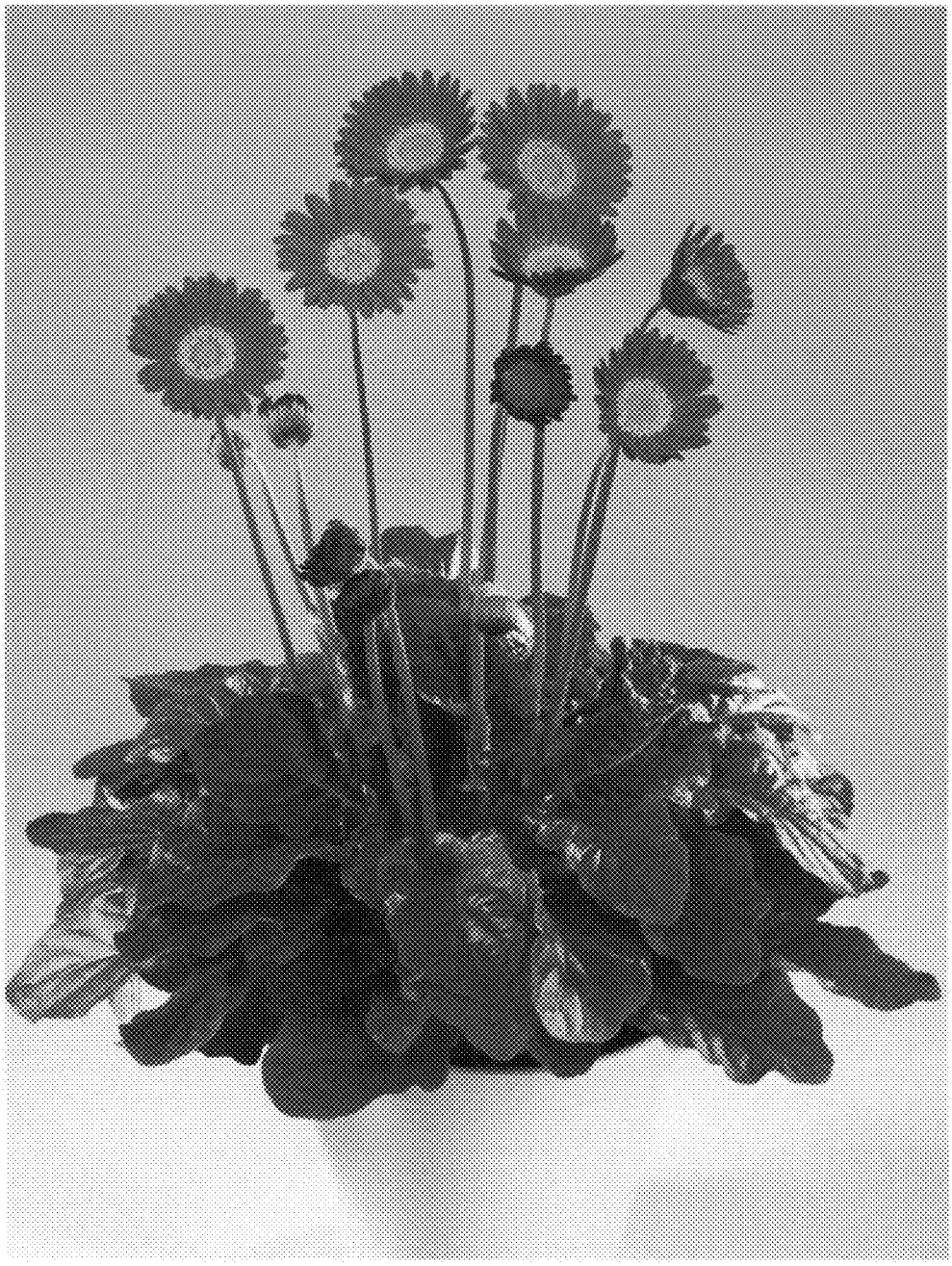

* * * * *